(12) United States Patent
Grayson

(10) Patent No.: US 8,465,440 B1
(45) Date of Patent: Jun. 18, 2013

(54) URINE COLLECTION SYSTEM

(76) Inventor: Darlene Grayson, Massapequa, NY (US)

( * ) Notice: Subject to any disclaimer, the term of this patent is extended or adjusted under 35 U.S.C. 154(b) by 0 days.

(21) Appl. No.: 13/238,560

(22) Filed: Sep. 21, 2011

(51) Int. Cl.
*A61B 5/00* (2006.01)
*A61B 5/20* (2006.01)

(52) U.S. Cl.
USPC .......... 600/575; 600/573; 600/574; 604/317; 604/322; 604/329; D24/122; D24/128; D24/224; D24/227

(58) Field of Classification Search
USPC .. 600/573, 574; 604/317, 322, 329; D24/122, D24/128, 224, 227
See application file for complete search history.

(56) References Cited

U.S. PATENT DOCUMENTS

| | | | | |
|---|---|---|---|---|
| 4,244,920 A | * | 1/1981 | Manschot et al. | 422/557 |
| 4,666,197 A | * | 5/1987 | Watson et al. | 294/31.2 |
| 4,696,067 A | | 9/1987 | Woodward | |
| D306,648 S | * | 3/1990 | Jones et al. | D24/128 |
| 5,147,342 A | * | 9/1992 | Kane et al. | 604/356 |
| D334,804 S | * | 4/1993 | Jones et al. | D24/128 |
| D335,176 S | * | 4/1993 | Jones et al. | D24/128 |
| D335,178 S | * | 4/1993 | Jones et al. | D24/128 |
| D335,179 S | * | 4/1993 | Jones et al. | D24/128 |
| D335,180 S | * | 4/1993 | Jones et al. | D24/128 |
| 5,202,094 A | * | 4/1993 | Jones et al. | 422/561 |
| D335,346 S | * | 5/1993 | Jones et al. | D24/128 |
| D335,708 S | * | 5/1993 | Jones et al. | D24/128 |
| D338,064 S | | 8/1993 | Jones et al. | |
| D341,883 S | * | 11/1993 | Jones et al. | D24/128 |
| D353,669 S | * | 12/1994 | Jones et al. | D24/122 |
| D357,066 S | | 4/1995 | Jones et al. | |
| 5,445,292 A | * | 8/1995 | Slomski et al. | 141/331 |
| D364,458 S | * | 11/1995 | Jones et al. | D24/128 |
| 5,492,220 A | * | 2/1996 | Estay | 206/363 |
| D368,135 S | * | 3/1996 | Vasai | D24/122 |
| 5,558,840 A | * | 9/1996 | Jones et al. | 422/561 |
| D379,655 S | * | 6/1997 | Savignac | D24/122 |
| D398,993 S | * | 9/1998 | Jones | D24/122 |
| D399,007 S | * | 9/1998 | Jones et al. | D24/227 |
| D408,913 S | * | 4/1999 | Jones | D24/227 |
| D449,685 S | * | 10/2001 | Morrison | D24/128 |
| 6,485,438 B1 | | 11/2002 | Minue | |
| 6,485,691 B1 | | 11/2002 | Jones | |
| 6,719,951 B1 | | 4/2004 | Griffith | |
| 6,799,694 B1 | | 10/2004 | Scott | |
| 6,837,472 B1 | * | 1/2005 | Beutz | 248/312 |
| 6,973,678 B2 | * | 12/2005 | Jones | 4/144.1 |
| 7,128,352 B1 | * | 10/2006 | Phippen | 294/1.5 |
| D579,557 S | * | 10/2008 | Washington | D24/122 |
| D593,206 S | * | 5/2009 | Kopoian | D24/227 |
| D610,700 S | | 2/2010 | Khoury | |
| D654,598 S | * | 2/2012 | Hooper | D24/227 |
| 2002/0169395 A1 | * | 11/2002 | Huang | 600/574 |

(Continued)

FOREIGN PATENT DOCUMENTS

WO    WO 9952442 A1 * 10/1999

*Primary Examiner* — Sean Dougherty

(57) ABSTRACT

A urine collection system having an elongated shaft with a first end and a second end, a first ring on the first end of the shaft, and a handle on the second end of the shaft, wherein a urine cup is removably held in the first ring, wherein the shaft is rigid, wherein the handle is a second ring, wherein the first ring and the second ring occupy the same planar surface, and wherein the first ring has a diameter larger than that of the second ring.

5 Claims, 2 Drawing Sheets

(ISO View)

U.S. PATENT DOCUMENTS

2008/0140032 A1* 6/2008 O'Malley ............... 604/322
2008/0199366 A1* 8/2008 Masters ............... 422/104
2009/0076413 A1* 3/2009 Robles ............... 600/573
2009/0118642 A1   5/2009 Washington

* cited by examiner (Top View)

(Front View)

(ISO View)

(Alternative Embodiment)

URINE COLLECTION SYSTEM

FIELD OF THE INVENTION

The present invention is directed to a system with a holder and cup designed to help a user during the urine collection process.

BACKGROUND OF THE INVENTION

Obtaining urine samples can be particularly difficult and messy. The present invention features a urine collection system. The system of the present invention helps a user easily and comfortably collect urine in a clean and sanitary manner. For example, the system helps prevent spillage, helps prevent urine from getting on the user's hands and clothing, and helps a user avoid touching the toilet seat.

SUMMARY

The present invention features a urine collection system. In some embodiments, the urine collection system comprises an elongated shaft having a first end and a second end; a first ring disposed on the first end of the shaft; and a handle disposed on the second end of the shaft.

In some embodiments, the system further comprises a urine cup removably held in the first ring. In some embodiments, the shaft is rigid. In some embodiments, the handle is a second ring. In some embodiments, the first ring and the second ring occupy the same planar surface. In some embodiments, the first ring has a diameter larger than that of the second ring.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

DESCRIPTION OF PREFERRED EMBODIMENTS

Figure 1:
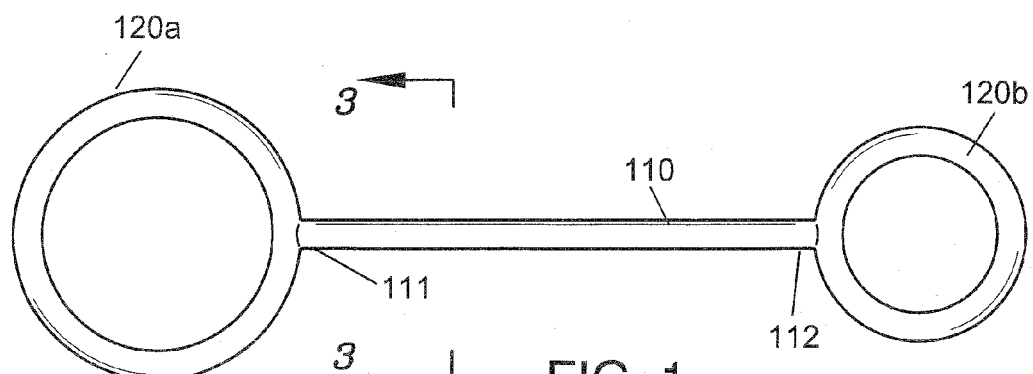
FIG. 1 is a top view of the system of the present invention.
Figure 2:
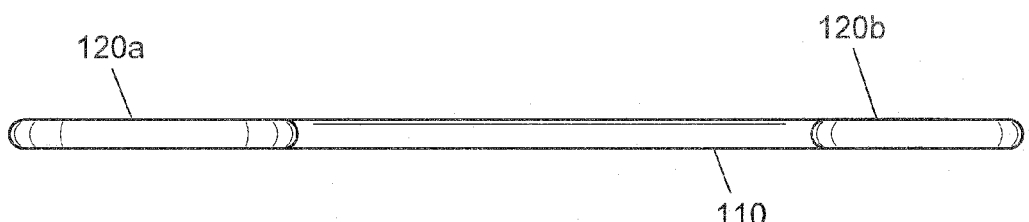
FIG. 2 is a side view of the system of the present invention.
Figure 3:
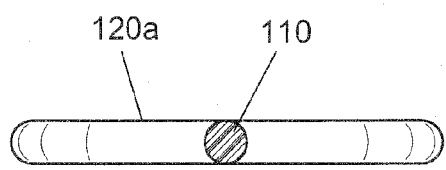
FIG. 3 is a side cross sectional view of the system of FIG. 3.
Figure 4:
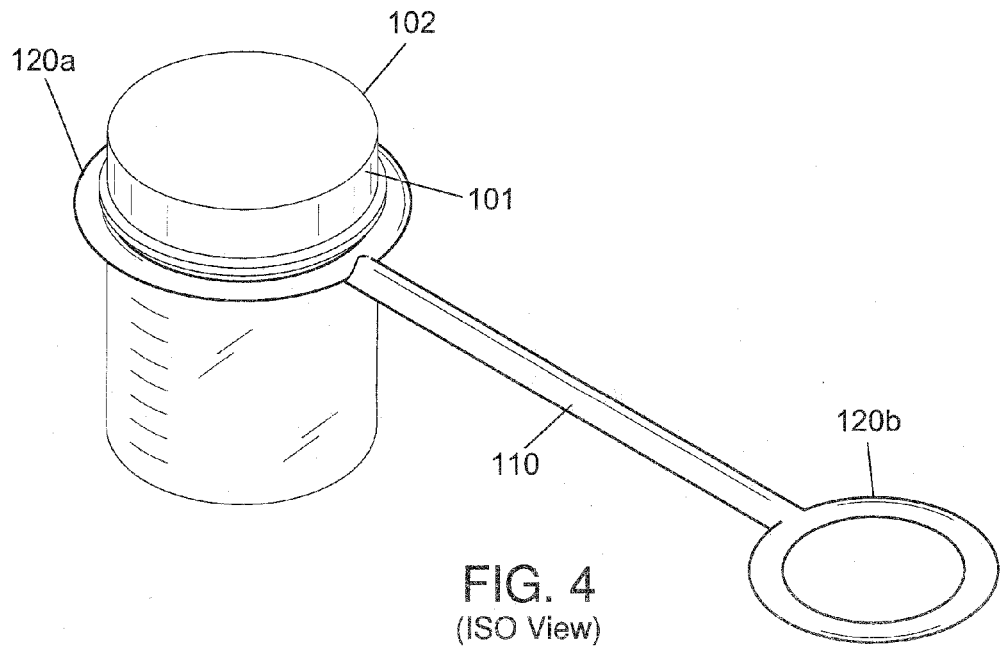
FIG. 4 is a perspective view of the system of the present invention.
Figure 5:
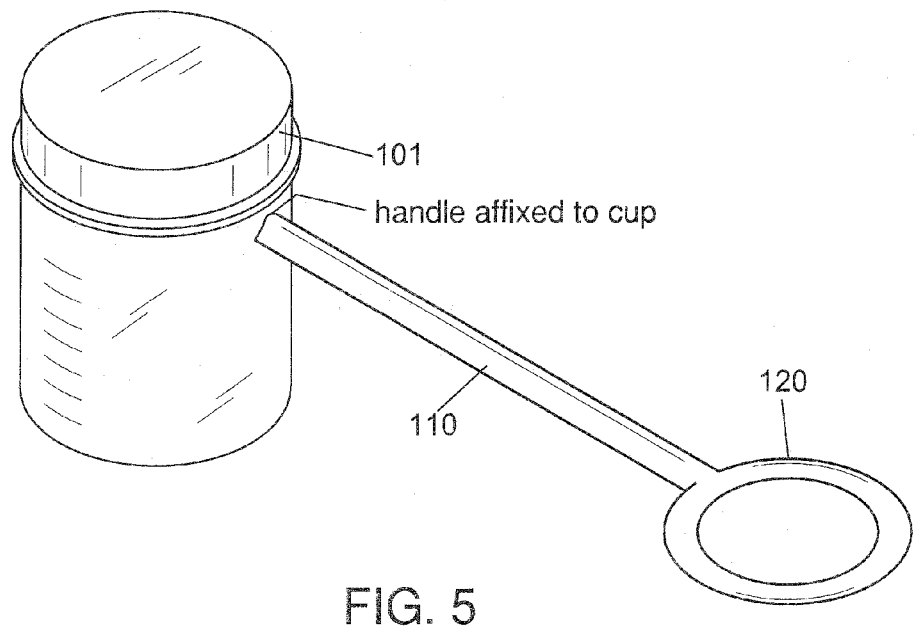
FIG. 5 is a perspective view of an alternative embodiment of the present invention.

Referring now to FIGS. 1-5, the present invention features a urine collection system 100. The system 100 comprises an elongated shaft 110 having a first end 111 and a second end 112. In some embodiments, the shaft 110 is rigid.

Disposed on the first end 111 of the shaft 110 is a first ring 120a. Disposed on the second end 112 of the shaft 110 is a handle 120b (e.g., a second ring). In some embodiments, the first ring 120a has a diameter larger than that of the second ring. The rings 120 may occupy the same planar surface. The shaft 110 has uniform width along the shaft length, wherein the width is smaller than the diameters of both the first and second rings.

The first ring 120a is adapted to hold a urine cup 101. For example, a urine cup 101 can be inserted into the center portion of the first ring 120a. Urine cups are well known to one of ordinary skill in the art and are commonly used in the medical industry. For example, urine cups 101 generally comprise a lip near the top where the lid 102 is attached. The lip of the urine cup 101 rests on the first ring 120a of the present invention, holding the cup 101 in place (e.g., see FIG. 4).

To use the system 100, a user inserts a urine cup 101 into the first ring 120a (with the lid 102 removed). The user holds on to the handle 120b (e.g., second ring) and, while sitting on a toilet, positions the cup under her urethra.

The handle 120b is not limited to a second ring. In some embodiments, the handle 120b on the second end 112 of the shaft 110 is any other appropriate component that allows a user to hold the shaft 110.

In some embodiments, the system 100 comprises a shaft 110 with a urine cup 101 directly attached to the first end 111 of the shaft 110 (e.g., see FIG. 5), as opposed to a first ring 120a.

The system 100 of the present invention may be constructed in a variety of sizes. For example, in some embodiments, the shaft 110 is between about 4 to 6 inches in length. In some embodiments, the shaft 110 is between about 6 to 8 inches in length. In some embodiments, the shaft 110 is between about 8 to 10 inches in length. In some embodiments, the shaft 110 is more than about 10 inches in length.

As used herein, the term "about" refers to plus or minus 10% of the referenced number. For example, an embodiment wherein the shaft 110 is about 10 inches in length includes a shaft 110 that is between 9 and 11 inches in length.

Without wishing to limit the present invention to any theory or mechanism, it is believed that the system 100 of the present invention is advantageous because the system 100 comprises a handle (e.g., ring shaped) that can be used as a secondary holder for a smaller cup (e.g., the system 100 holds two cups with different diameters). The handle is long and is ring-shaped.

The disclosures of the following U.S. patents are incorporated in their entirety by reference herein: U.S. Pat. No. 4,696,067; U.S. Design Pat. No. D338064; U.S. Design Pat. No. D357066; U.S. Pat. No. 6,485,438; U.S. Pat. No. 6,485,691; U.S. Pat. No. 6,719,951; U.S. Pat. No. 6,799,694; U.S. Design Pat. No. D610700; U.S. Patent Application No. 2009/0118642.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims.

The reference numbers recited in the below claims are solely for ease of examination of this patent application, and are exemplary, and are not intended in any way to limit the scope of the claims to the particular features having the corresponding reference numbers in the drawings.

What is claimed is:
1. A urine collection system (100) comprising:
  (a) an elongated shaft (110) having a first end (111) and a second end (112); a first ring (120a) disposed on the first end (111) of the shaft (110); and a handle (120b) dis- posed on the second end (112) of the shaft (110), wherein the handle (120*b*) is a second ring, wherein the shaft (110) has uniform width along the shaft length, wherein the width is smaller than the diameters of both the first and second rings; and (b) a first urine cup (101) having a lip, and a second urine cup having a lip, wherein the first and second urine cups are inserted into the first ring and second ring, respectively, wherein the lip of the cups rests on the respective rings.

2. The system (100) of claim 1, wherein the shaft (110) is rigid.

3. The system (100) of claim 1, wherein the first ring (120*a*) and the second ring occupy the same planar surface.

4. The system (100) of claim 1, wherein the first ring (120*a*) has a diameter larger than the diameter of the second ring (120*b*).

5. A urine collection system (100) consisting of:

(a) an elongated shaft (110) having a first end (111) and a second end (112) a first ring (120*a*) disposed on the first end (111) of the shaft (110); and a handle (120*b*) disposed on the second end (112), of the shaft (110), wherein the handle (120*b*) is a second ring, wherein the shaft (110) has uniform width along the shaft length, wherein the width is smaller than the diameters of both the first and second rings; and (b) a first urine cup having a lip, and a second urine cup having a lip, wherein the first and second urine cups are inserted into the first ring and second ring, respectively, wherein the lip of the cups rests on the respective rings;

wherein the first ring (120*a*), and the second ring occupy the same planar surface;

wherein the first ring (120*a*) has a diameter larger than the diameter of the second ring (120*b*).

* * * * *